United States Patent [19]

Mortenson

[11] Patent Number: 5,211,163

[45] Date of Patent: May 18, 1993

[54] METHOD FOR REDUCING SCOLIOSIS

[76] Inventor: Dale E. Mortenson, 1101 Ohio Avenue, Lynn Haven, Fla. 32444

[21] Appl. No.: 579,841

[22] Filed: Sep. 7, 1990

Related U.S. Application Data

[63] Continuation-in-part of Ser. No. 439,183, Nov. 20, 1989, abandoned.

[51] Int. Cl.⁵ .................................................. A61F 5/02
[52] U.S. Cl. ................................... 128/781; 128/779; 482/105; 602/19
[58] Field of Search ............... 272/118, 119, 143; 128/68–75, 78, 779, 780, 781, 782

[56] References Cited

U.S. PATENT DOCUMENTS

| | | | |
|---|---|---|---|
| 3,838,853 | 10/1974 | Fredenhagen | 272/119 X |
| 3,888,245 | 6/1975 | Berntson et al. | 272/119 X |
| 4,014,398 | 3/1977 | Gresko | 128/782 X |
| 4,093,214 | 6/1978 | Coker et al. | 272/118 |
| 4,122,840 | 10/1978 | Tsuchita et al. | 128/779 |
| 4,394,012 | 7/1983 | Egbert et al. | 272/119 |
| 4,494,533 | 1/1985 | Sgroi et al. | 128/75 |
| 4,674,484 | 6/1987 | Kott | 128/75 |
| 4,684,123 | 8/1987 | Fabrt | 272/119 |

FOREIGN PATENT DOCUMENTS 218063  7/1967  Sweden .................................. 272/119

Primary Examiner—Robert Bahr
Attorney, Agent, or Firm—Macdonald J. Wiggins

[57] ABSTRACT

A person having functional scoliosis is weighed on a bilateral scale, and the amount of bilateral unbalance calculated. A corrective weight is calculated, and installed in pockets of a harness that supports the weight below the armpit of the person. The harness includes a chest strap, a shoulder strap, and a plurality of weight pockets. A plurality of thin lead weights is provided to be selectively inserted into the pockets. A pocket element may be provided that is attachable to a brassiere strap.

10 Claims, 2 Drawing Sheets

METHOD FOR REDUCING SCOLIOSIS

This application is a continuation-in-part of application Ser. No. 07/439,183 filed Nov. 20, 1989, now abandoned.

BACKGROUND OF THE INVENTION

1. Field of the Invention

The present invention relates to devices for correcting abnormalities of the spine, and more particularly to a harness for improvement and correction of functional scoliosis.

2. Description of the Prior Art

Scoliosis is an abnormal lateral curvature of the spine. Structural scoliosis refers to a structural abnormality in the anatomical structure of the spine, such as wedging of the vertebral body. Functional scoliosis is a condition caused by an unbalance in the development of the muscles on either side of the spine. For example, persons carrying loads on one side of the body, such as mail carriers, may develop this condition. Functional scoliosis is common in females, believed to be caused by differences in the size and weight of the breasts. The condition often appears at puberty and may progress for the life of the person, with the most rapid progression occurring before the closure of the epiphyseal plates as the body attempts to compensate and adapt to the weight differential.

Prior art attempts to treat functional scoliosis have utilized rigid braces. One disadvantage is that young persons object to such braces and may resist continuing to wear the devices. More importantly, braces may not permit the body to naturally overcome the problem, since the weaker muscles are not developed.

Thus, there is a need for a device and method without the use of braces that will improve functional scoliosis, and will encourage strengthening of the weaker muscles involved in the condition. It has been found that functional scoliosis can be moderated or corrected by the present invention.

SUMMARY OF THE INVENTION

The present invention treats functional scoliosis in a patient by adding weight equal to the differential weight that is causing the condition. According to the method of the invention, a patient is examined and the difference between the lateral weight distribution is measured by a scale having two weight sensors. The scale weighs the patient with one foot on each sensor, thereby providing the total weight and the weight per foot. Patients have been found to have differences of over ten pounds in their bilateral weights.

After determination of the differential weight, a harness having a plurality of pockets is prepared and worn under the patients clothing. It is not necessary that the differential weight be used since the invention provides a leverage action, and a small weight can change the center of gravity of the patient's body toward the side of the weight. Thus, weights of one-quarter to one pound have been found to be sufficient.

Thus, small test weights are placed in the harness pockets, and the bilateral weight observed. When equal, the effect on the spine may then be observed by appropriate X-rays.

A harness may be custom designed for an individual patient. In one embodiment of the invention suitable for female patients, a set of weight pockets is provided that may be attached to the side of a brassiere.

It is therefore a principal object of the invention to provide a method and apparatus for correcting or improving functional scoliosis of a patient.

It is another object of the invention to provide a method of determining an amount of lateral unbalance in a patient having functional scoliosis.

It is still another object of the invention to provide a harness having calibrated weights to be worn by a patient having functional scoliosis that is wearable beneath the clothing.

These and other objects and advantages of the invention will become apparent from the following detailed description when read in conjunction with the drawings.

BRIEF DESCRIPTION OF THE DRAWINGS

FIG. 3 is a an alternative embodiment of a weight pouch that may be attached to a brassiere or the like.

DETAILED DESCRIPTION OF THE PREFERRED EMBODIMENT

Figure 1:
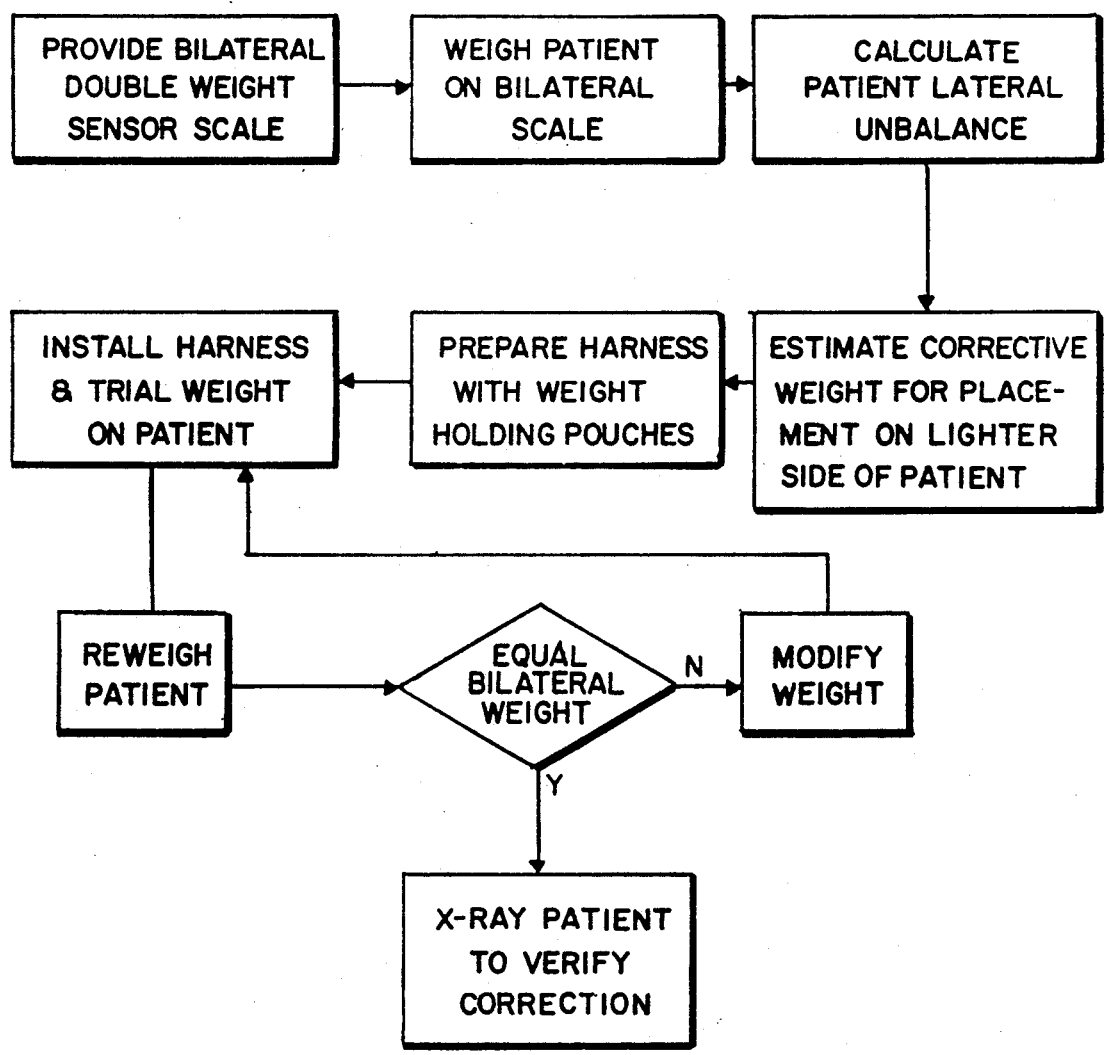
FIG. 1 is a flow diagram of the method of the invention.

The method of the invention for correcting or reducing functional scoliosis is shown in the flow diagram of FIG. 1. An unbalanced body condition of a patient causing the condition is determined by providing a scale having a platform for each foot and a weight sensor associated with each platform. The lateral weight unbalance of the patient is calculated from the scale readings. Next, an estimate is made for a trial corrective weight to be installed on the lighter side of the patient. A harness is prepared to fit the patient, and having weight pouches on the lighter side of the patient. The estimated trial weight is inserted in the pouches, and the harness is installed on the patient. The patient is reweighed on the bilateral scale to determine the amount of correction achieved with the trial weight. If a desired balance is not achieved, the weight is modified and the patient reweighed. When an equal bilateral weight is achieved, the patient may be x-rayed to verify the effect of the procedure on the scoliosis condition.

If, when a balanced condition is achieved and insufficient correction of the scoliosis is obtained, a spinal adjustment may be performed by a qualified practitioner to further improve the patient. This procedure, known as an atlas orthogonal adjustment, produces a mechanical reduction and decompression of specific joint subluxations, displacements, and misalignments. The procedure can bring about an orthogonal, anatomical, structural balance to the occipital atlas-axis synovial joint complex.

Figure 2:
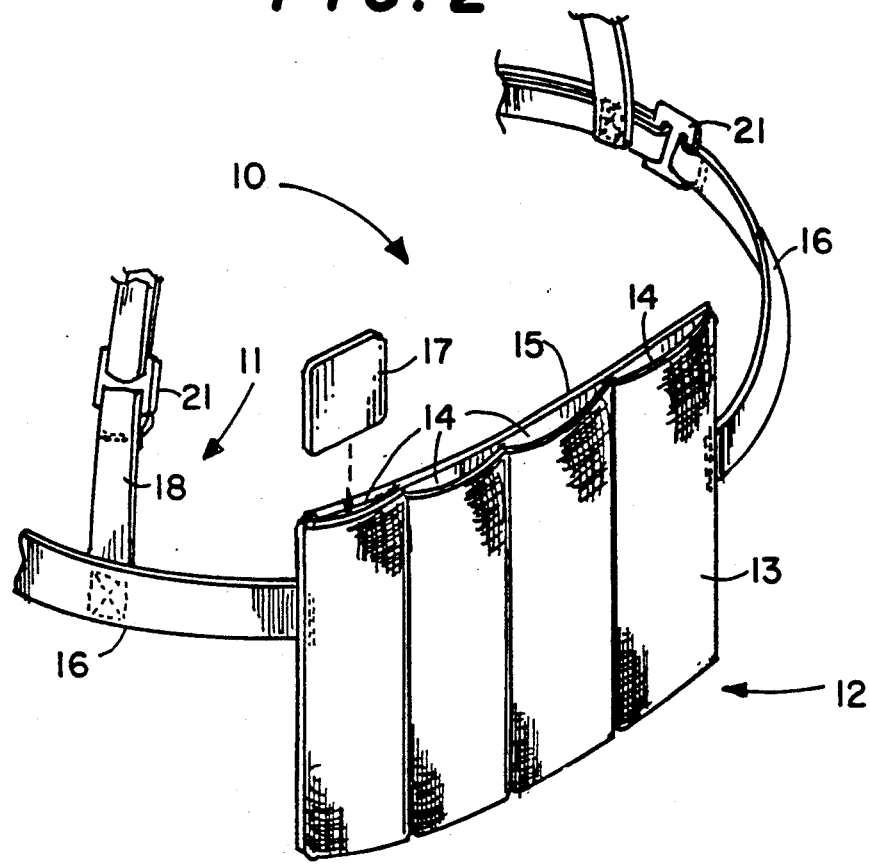
FIG. 2 is a perspective view of a scoliosis harness, typical weight, and weight pouch element in accordance with the invention.

Details of the weight pouch harness 10 of the invention are shown in FIG. 2. Pouch element 12 includes a plurality of pockets 14 formed from a front panel 13, and a back panel 15, made of a flexible fabric-type material. The width of pockets 14 is selected to accept flat weights 17. A typical weight 17 may weigh one-half ounce, permitting adjustment of the total weight for a patient within practical steps. Weight 17 has smooth, rounded edges to prevent discomfort to a patient.

Pouch element 12 may be attached to a belt 16, shown in partial view, which may pass under the arm pits of the patient and adjusted to fit by a buckle 21, or the like. An adjustable shoulder strap 18 supports belt 16 and pouch element 12.

Figure 3:
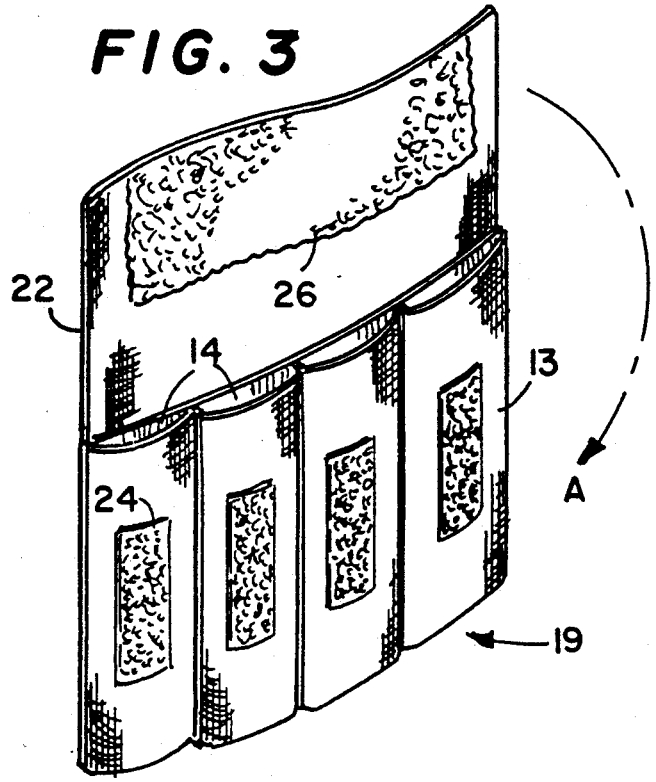

An alternative pouch element 19 is shown in perspective view in FIG. 3. Pockets 14 are formed as in pouch element 12, except that back panel 22 is extended above pockets 14. The front surfaces of front panel 13 includes a plurality of hook and loop fastener strips 24 attached thereto. The front face of the extension of back panel 22 includes a hook and loop fastener strip 26, complementary to strips 24, attached thereto.

Pouch element 19 may be used with a brassiere by folding extension 22 over the brassiere strap and coupling to strips 24, thereby supporting the weights without a separate harness. As may be noted, pouch element 19 may be used with brassiere straps of various widths. Other types of fasteners, such as snaps, may be used with Pouch element 19.

As will now be recognized, a weight harness has been disclosed for use with a method of correcting functional scoliosis that is effective in correcting or reducing the condition. The following case history is for a typical application of the invention.

History

A white female in her early 20's had an clearly noticeable scoliosis, and experienced headaches, and neck and back pain.

The patient's posture resulted in both left shoulder and left ear being high.

Treatment

Bilateral weight measurements of the patient were made in which the right weight was 65 pounds, and the left side weight was 75 pounds. Experimentally, it was determined that 7 ounces of weight added to the left side resulted in the shoulders being even and level. The left ear was still high, indicating a slight spinal misalignment. An atlas orthogonal adjustment was made which corrected the unevenness of the ears.

Results

Review of X-rays taken without the added weight indicated that the weight-bearing line drawn through the center of C-2 was shifted to the right, and the scoliosis, as measured with Cobb's angle, was 15 degrees. X-rays taken with the corrective weight showed that the weight-bearing line had moved 5 mm to the left, and the scoliosis was reduced to 6 degrees.

For about one year since treatment and continued use of the weight device of the invention, the patient has been free of back pain, and has had no observable postural abnormalities Although a specific method and weight-holding harness device has been described, modifications thereto may be made without departing from the spirit and scope of the invention.

I claim:

1. A method for reducing functional scoliosis of a person comprising the steps of:
    a) determining the lateral unbalanced weight of the person;
    b) estimating the value of a corrective weight for placement on a lighter side of the patient;
    c) providing a harness for holding the estimated weight;
    d) installing the harness and estimated weight on the person; and
    e) verifying an equal bilateral weight of the person.

2. The method as defined in claim 1 in which step a) includes the steps of:
    f) providing a bilateral scale having a double weight sensor;
    g) weighing the person on the bilateral scale; and
    h) calculating the bilateral unbalance weight.

3. The method as defined in claim 2 in which step e) includes the steps of:
    i) reweighing the person on the bilateral scale; and
    j) modifying the corrective weight; and
    k) repeating steps i) and j) until equal bilateral weight measurements are obtained.

4. The method as defined in claim 1 in which step a) includes the further step of x-raying the person for verifying reduction of the scoliosis.

5. The method as defined in claim 1 in which step c) includes the step of:
    providing a harness having a chest encircling strap, and a shulder strap, a plurality of pockets attached to said chest strap, and located therealong to be disposed below one armpit of the person; and a plurality of weights adapted to be selectively inserted into said pockets.

6. The method as defined in claim 5 in which said chest strap and said shulder strap each include length adjustment means.

7. The method as defined in claim 5 in which said weights are formed of lead.

8. The method as defined in claim 7 in which said weights have an essentially thin, rectangular shape.

9. The method as defined in claim 1 in which step c) includes the step of:
    providing a pouch element having a back panel, a plurality of pockets attached to a face of said back panel, said panel extending above upper edges of said pockets, first fastening means attached to an upper edge of said back panel, second fastening means mating with said first fastening means attached to a front surface of said pockets wherein said upper edge of said back panel is foldable over a brassiere strap for fastening said first fastening means to said second fastening means; and a plurality of thin, flat weights selectively insertable in said pockets.

10. The method as defined in claim 9 in which:
    said first fastening means is a first hook and loop type fastener; and
    said second fastening means is a second hook and loop type fastener complementary to said first hook and loop type fastener.

* * * * *